United States Patent
McQuinn

[11] Patent Number: 5,113,860
[45] Date of Patent: May 19, 1992

[54] NON-INVASIVE TRANSMUCOSAL DRUG LEVEL MONITORING METHOD

[75] Inventor: Roy L. McQuinn, St. Paul, Minn.

[73] Assignee: Minnesota Mining and Manufacturing Company, St. Paul, Minn.

[21] Appl. No.: 669,775

[22] Filed: Mar. 15, 1991

[51] Int. Cl.$^5$ ................................................ A61B 5/00
[52] U.S. Cl. .................................................... 128/632
[58] Field of Search ............. 128/632, 637, 640, 643, 128/743, 749, 897–899; 604/19, 289, 290, 304, 312, 313, 327, 328

[56] References Cited

U.S. PATENT DOCUMENTS

| | | |
|---|---|---|
| 3,339,546 | 9/1967 | Chen . |
| 3,552,929 | 1/1968 | Fields et al. .................... 128/632 |
| 4,153,661 | 5/1979 | Ree et al. . |
| 4,190,060 | 2/1980 | Greanleaf et al. ................ 604/312 |
| 4,253,460 | 3/1981 | Chen et al. . |
| 4,321,252 | 3/1982 | Keith et al. ..................... 424/28 |
| 4,373,519 | 2/1983 | Errede et al. . |
| 4,444,193 | 4/1984 | Fogt et al. ...................... 128/632 |
| 4,706,676 | 11/1987 | Peck ............................... 128/632 |
| 4,740,365 | 4/1988 | Yukimatsu et al. . |
| 4,772,470 | 9/1988 | Inoue et al. . |
| 4,795,436 | 1/1989 | Robinson . |
| 4,906,378 | 3/1990 | Hagen et al. . |
| 4,909,256 | 3/1990 | Peck ............................... 128/632 |
| 4,960,467 | 10/1990 | Peck ............................... 128/632 |
| 4,981,145 | 1/1991 | Goldstein ......................... 604/312 |
| 5,056,521 | 10/1991 | Parsons et al. ................... 128/898 |

FOREIGN PATENT DOCUMENTS 9002511  3/1990  World Int. Prop. O. ......... 128/632

*Primary Examiner*—C. Fred Rosenbaum
*Assistant Examiner*—Sharon Finkel
*Attorney, Agent, or Firm*—Gary L. Griswold; Walter N. Kirn; Douglas E. Reedich

[57] ABSTRACT

Non-invasive transmucosal drug monitoring methods involving devices comprising an acid-functional polymeric resin dispersed substantially throughout a hydrophobic support matrix. The device when adhered to a mucosal surface can absorb some chemicals in amounts proportional to the actual blood levels of the chemicals.

30 Claims, No Drawings

NON-INVASIVE TRANSMUCOSAL DRUG LEVEL MONITORING METHOD

BACKGROUND OF THE INVENTION

1. Field of the Invention

This invention relates to compositions that adhere to oral mucosa. In another aspect this invention relates to methods, particularly non-invasive methods, of monitoring the level of compounds in the blood.

2. Description of the Related Art

Conventional methods of monitoring blood levels of chemicals involve analysis of blood or urine. Some chemicals such as ethanol can pass through the skin and can be monitored in a non-invasive fashion by trapping in a patch or other device on the skin. However, for most chemicals the low permeability of skin precludes the use of such a transdermal system, and analysis of blood or urine is the only practical way to monitor blood levels.

Many drugs are known to be capable of transmucosal delivery. Sustained release adhesive bandages, patches, and the like that contain drugs and adhere to mucosal surfaces are also known to the art. Polyacrylic acids and polyisobutylenes have been disclosed as components of such adhesives. For example, U.S. Pat. No. 3,339,546 (Chen) discloses a bandage that is said to adhere to moist surfaces of the oral cavity and comprises a medicament and a hydrocolloid incorporated in a natural or synthetic gum-like substance. Carboxypolymethylene (i.e., polyacrylic acid) is among the hydrocolloids disclosed and polyisobutylene is among the gum-like substances disclosed.

U.S. Pat. No. 4,795,436 (Robinson) discloses a composition including a bioadhesive and a treating agent. The bioadhesive is a water-swellable but water insoluble, fibrous, crosslinked, carboxy-functional polymer containing (a) a plurality of repeating units of which at least about 80% contain at least 1 carboxy functionality, and (b) about 0.05 to about 1.5% of a cross-linking agent substantially free from polyalkenyl polyether. The specifically excluded type of crosslinker is said to be the type used in CARBOPOL TM 934 resin (commercially available from B. F. Goodrich, Specialty Chemicals and Polymers Division, Cleveland, Ohio). CARBOPOL TM 934 resin is said to be water soluble and therefore undesirable as a bioadhesive in the Robinson composition.

U.S. Pat. No. 4,253,460 (Chen et al.) discloses an adhesive composition consisting of a mixture of a hydrocolloid gum, a pressure sensitive adhesive, and a cohesive strengthening agent. The pressure sensitive adhesive component can be a mixture of three to five parts of a polyisobutylene with a viscosity average molecular weight of about 36,000 to about 53,000 and one part of an elastomer such as a polyisobutylene with a viscosity average molecular weight of about 1,150,000 to about 1,600,000.

U.S. Pat. No. 4,740,365 (Yukimatsu et al.) discloses a sustained-release preparation comprising an active ingredient and a mixture of two polymer components, the first of which comprises one or more polymers selected from polyacrylic acid and a pharmaceutically acceptable salt thereof, and the second being selected from the group consisting of polyvinylpyrrolidone, polyvinyl alcohol, polyethylene glycol, alginic acid, and a pharmaceutically acceptable salt of alginic acid. CARBOPOL TM resins are among the polymers said to be suitable members of the first-mentioned class of polymers.

U.S. Pat. No. 4,772,470 (Inoue, et al.) discloses an oral bandage comprising a mixture of a polyacrylic acid and a vinyl acetate polymer in a compatible state. This bandage is said to exhibit strong adhesion of long duration when applied to oral mucosa or teeth.

None of the above-mentioned compositions or devices have any disclosed utility with respect to the monitoring of drug levels in the blood of a patient.

SUMMARY OF THE INVENTION

This invention provides methods of measuring the blood level of a drug in a mammal, comprising the steps of:

a) adhering a device to a mucosal surface of a mammal which device comprises:
  (i) a particulate polymeric resin comprising at least about 55% by weight of carboxylic acid moieties based on the total weight of the polymeric resin, and
  (ii) about 10 to about 200 parts by weight of a hydrophobic support matrix, based on 100 parts by weight of the resin,
wherein the resin is dispersed substantially throughout the support matrix, and which is substantially free of drug, contains less than about 9% water by weight based on the weight of the polymeric resin, exhibits substantially no instantaneous adhesion to dry skin, and adheres to a mucosal surface;

b) allowing the device to remain adhered for a time sufficient for the device to absorb the drug in an amount proportional to the blood level of the drug;

c) removing the device;

d) measuring the amount of the drug in the device; and e) correlating the amount of the drug in the device to the blood level of the drug.

The methods of the invention can be used to monitor blood levels of a drug across the oral or vaginal mucosa or other mucosal surfaces and thus provides a non-invasive alternative to blood tests or urine screens. The methods of the invention find use in monitoring compounds such as drugs of abuse, which are commonly monitored by a urine screen that in many instances detects only urinary metabolites. Such metabolites are sometimes produced not only by drugs of abuse but also by food, over-the-counter medications, or other legitimate sources. Since the methods of the invention allow assay without the complication of renal metabolites, the invention can decrease the likelihood of false positive results. A device used in the methods of the invention is also soft and conformable such that it can be worn comfortably by the user.

DETAILED DESCRIPTION OF THE INVENTION

The polymeric resin component of a device used in the methods of this invention comprises at least about 55% by weight of carboxylic acid moieties based on the total weight of the resin. Suitable carboxylic acid-containing monomers include acrylic acid, maleic acid, itaconic acid, citraconic acid, methacrylic acid, and the like, and combinations thereof. Acrylic acid is preferred. The polymeric resin can also comprise minor amounts (e.g., less than about 20 percent by weight based on the total weight of all monomers in the polymer) of comonomers that are polymerizable with the carboxylic acid-containing monomer, such as methyl vinyl ether, lower alkyl (meth) acrylates, and the like.

Linear polyacrylic acid resins with a molecular weight between about 400,000 and about 5,000,000 have been found to be suitable for use in a composition of the invention. More preferred, however, are crosslinked resins. Most preferred resins include those comprising polyacrylic acid with a molecular weight between about 750,000 and about 3,000,000, crosslinked with about 0.75% to about 2% by weight, based on the total weight of the resin, of a polyalkenyl polyether such as an allyl ether of sucrose or an allyl ether of pentaerythritol. Particularly preferred resins of this type include the resins available under the trade designation CARBOPOL TM (e.g., CARBOPOL TM resins 910, 934, 934P, 941, 951, and 1342 from B.F. Goodrich Co., Specialty Polymers and Chemical Division, Cleveland, Ohio). CARBOPOL TM 934P resin is most preferred, as it is generally recognized as acceptable for pharmaceutical applications. Another suitable resin is "polycarbophil", a material commercially available from A. H. Robins Co., Richmond, Va., and described in USP XX as a polyacrylic acid crosslinked with divinylglycol.

A polyacrylic acid resin or a crosslinked resin such as those enumerated above can be partially neutralized by a base of an alkali metal, or by a base of a divalent or trivalent metal (e.g., $Zn^{+2}$, $Ca^{+2}$, $Mg^{+2}$, or $Al^{+3}$). Basic polyamines such as Eudragit TM E (a copolymer of dimethylaminoethyl methacrylate and neutral methacrylates, available from Rohm Pharma, Weiterstadt, Germany) are also suitable for use in neutralizing a resin. In such a resin, up to about 30% of the carboxylic acid moieties in the resin can be neutralized by a base. Preferred bases include $Al(OH)_3$ and $Ca(OH)_2$.

It is desirable to keep the level of moisture low. A mucoadhesive device has a water content of less than about 10% by weight, preferably less than about 6%, more preferably less than about 4% by weight, and most preferably less than about 2% by weight based on the total weight of the resin. In order for the device to have the requisite low water content, the resin prior to incorporation in the device is preferably dried to the desired level and protected from ambient moisture. Once the resin is incorporated in a device, ambient moisture is no longer generally of concern, because the resin, which is generally hygroscopic, is protected from ambient moisture by the support matrix. A device can be stored for at least several months at ambient humidity without adversely affecting its mucoadhesive properties.

A resin preferably has a particle size less than about 100 $\mu$m preferably between about 1 $\mu$m and about 100 $\mu$m, more preferably about 1 $\mu$m to about 30 $\mu$m, and most preferably about 2 $\mu$m to about 10 $\mu$m.

By itself, a polymeric resin as described above generally possesses insufficient structural integrity and will disintegrate upon prolonged adhesion to a mucosal surface. Such acidic resins can also be irritating to mucosal tissue. To remedy these deficiencies, the resin is substantially dispersed throughout a hydrophobic support matrix.

The relative amounts of the polymeric resin and the hydrophobic support matrix can affect both the duration of adhesion and the drug absorption properties of a device. Generally a device comprises about 10 parts to about 200 parts, preferably about 10 parts to about 100 parts, and most preferably 15 to about 50 parts by weight of a hydrophobic support matrix, based on 100 parts by weight of the resin.

Suitable support matrices preferably are soft such that the ultimate device can be worn without significant discomfort to the user. Further, they are such that a device does not exhibit excessive cold-flow when stored at room temperature. The support matrix preferably has a surface energy of less than about 40 dyne/cm and more preferably has a surface energy of less than about 30 dyne/cm.

The support matrix can be in the form of an elastomeric component. Examples of materials suitable for use in an elastomeric component include: hydrocarbons such as block styrene-butadiene-styrene copolymers and block styrene-isoprene-styrene copolymers, such as those available from Shell Chemical Co. as Kraton TM rubbers, polyolefins such as polyisobutylenes, polybutadienes, butyl rubber (a copolymer of isobutylene and isoprene), and isoprene rubbers, e.g., polyisoprene (such as that available as LIR-50 from Arakawa Chemical Co., Chicago, Ill.); functionalized polyoefins such as functional polyisoprenes, e.g., carboxy-functional polyisoprenes (such as that available as LIR-410, also from Arakawa) and hydroxy-functional polyisoprenes (such as that available as LIR-506, Arakawa); and mixtures and blends of two or more of the foregoing.

Another class of material suitable for use in an elastomeric component includes acrylate elastomers. Suitable acrylate elastomers include polymers and copolymers comprising at least about 60 percent by weight based on the total weight of all monomers in the polymer of a hydrophobic monomeric acrylic or methacrylic acid ester of an alkyl alcohol, the alkyl alcohol containing 4 to 10 carbon atoms. Some such elastomers are disclosed in U.S. Pat. No. 4,751,087 (Wick) the disclosure of which is incorporated herein by reference. Particularly suitable are those acrylate copolymers containing A and B Monomers as follows: Monomer A is a hydrophobic monomeric acrylic or methacrylic acid ester of an alkyl alcohol, the alkyl alcohol containing 4 to 10 carbon atoms, preferably 8 carbon atoms. Examples of suitable A Monomers are n-butyl, n-pentyl, n-hexyl, isoheptyl, n-nonyl, n-decyl, isohexyl, isooctyl, 2-ethyloctyl, and 2-ethylhexyl acrylates. The most preferred A Monomer is isooctyl acrylate. Monomer B is a reinforcing monomer selected from the group consisting of acrylic acid; methacrylic acid; alkyl acrylates and methacrylates containing 1 to 3 carbon atoms in the alkyl group; acrylamide; methacrylamide; and lower alkyl-substituted acrylamides (i.e., the alkyl group containing 1 to 4 carbon atoms) such as tertiary-butyl acrylamide. The most preferred B Monomer is acrylamide. In such an elastomer, the A Monomer is preferably present in an amount by weight of about 80 percent to about 98 percent, and the B Monomer is preferably present in an amount by weight of about 2 to about 20 percent of the total weight of the monomers in the copolymer. While such acrylate copolymers per se are pressure-sensitive adhesives, when they are incorporated into a device, the device exhibits substantially no instantaneous adhesion to dry skin.

Hydrocarbons are preferred materials for use in an elastomeric component. Preferred hydrocarbon elastomeric components, particularly when the device is prepared by the solvent casting method set forth in detail below, include polyisobutylene mixtures comprising, based on the total weight of the polyisobutylene mixture, from about 5% to about 50%, preferably about 15% to about 25%, and most preferably about 20%, by weight of a polyisobutylene with a viscosity average molecular weight between about 500,000 and about 2,500,000, preferably about 1,250,000, and from about 50% to about 95%, preferably about 75% to about 85%, and most preferably about 80%, by weight of a polyisobutylene with a viscosity average molecular weight between about 40,000 and about 100,000, preferably about 53,000. Particularly preferred is an elastomeric component made by the solvent-casting method and consisting of about 80% by weight of VISTANEX ™ LM-MH polyisobutylene and about 20% by weight of VISTANEX ™ L-100 polyisobutylene.

In contrast to a solvent casting method, the milling process (set forth in detail below) can reduce substantially the molecular weight of the polymers that are used in the process. For example, preferred polyisobutylene elastomers in embodiments made by the milling process are made from the preferred polyisobutylenes enumerated above but they have molecular weights lower than the ranges set forth above. A particularly preferred elastomeric component for use when the milling method is employed is a polyisobutylene mixture made from about 60 to 100% by weight of a polyisobutylene with a viscosity average molecular weight of about 750,000 to about 1,500,000, most preferably about 900,000, and 0% to about 40% of a polyisobutylene with a viscosity average molecular weight of about 40,000 to about 100,000, most preferably about 53,000.

Individual polyisobutylenes suitable for use in the above-described elastomeric components include those commercially available from Exxon Chemical Co., Houston Tex., under the trade designation VISTANEX ™ polyisobutylene and those commercially available from BASF under the trade designation OPPANOL ™ polyisobutylene. Preferred polyisobutylenes include VISTANEX ™ LM-MH polyisobutylene (viscosity average molecular weight about 53,000), VISTANEX ™ L-80 polyisobutylene (viscosity average molecular weight about 900,000), and VISTANEX ™ L-100 polyisobutylene (viscosity average molecular weight about 1,250,000).

For purposes of the instant specification and claims, the term viscosity average molecular weight means Florey molecular weight as determined by the method set forth in "Food Chemicals Codex", 3rd Ed. page 469, 1981, National Academy Press, incorporated herein by reference.

An elastomeric component can also comprise a plasticizer such as mineral oil, silicone oil, corn oil, and the like. A particularly preferred elastomeric component of this type is a mixture comprising mineral oil and linear styrene-isoprene-styrene block copolymer such as that commercially available from Shell Chemical, Houston, Tex., under the trade designation KRATON ™ D1107 rubber. It is preferred that an elastomeric component of this type comprise from about 20 percent to about 40 percent, more preferably about 33 percent, by weight of mineral oil and correspondingly from about 60 percent to about 80 percent, more preferably about 67 percent, by weight of the block copolymer.

The support matrix can also be in the form of a polytetrafluoroethylene (PTFE) web. Such webs having particulate material substantially uniformly dispersed therein are disclosed in, e.g., U.S. Pat. Nos. 4,153,611 (Ree, et al.), 4,373,519 (Errede et al.), and 4,906,378 (Hagen et al.), the disclosures of which are incorporated herein by reference.

A device can contain other ingredients, for example excipients such as flavorings, dyes, surfactants, water-soluble or water-swellable fibrous reinforcers, and the like under circumstances and in amounts easily determined by those skilled in the art. Suitable surfactants include anionic surfactants (e.g., sodium lauryl sulfate); cationic surfactants (e.g., cetylpyridinium chloride); nonionic surfactants (e.g., polysorbate 80, polyoxyethylene 9-lauryl ether, glyceryl monolaurate); lipids (e.g., oleic acid); bile salts (e.g., sodium glycocholate, sodium taurocholate); and related compounds (e.g., sodium tauro-24,25-dihydrofusidate). Such ingredients can be dispersed substantially uniformly in the device or dispersed in any suitable gradient therein.

A device used in the methods of this invention is substantially free of drug, i.e., it contains no drug or if a drug is present (as will be the case, e.g., when a device has been adhered to a mucosal surface for a sufficient period of time, as described below in connection with the drug level monitoring methods of the invention) it is present in an amount substantially lower than a therapeutically effective amount.

A resin useful in a device can be prepared using conventional procedures and conventional laboratory equipment. For example, such resins can be prepared from acrylic acid and the appropriate crosslinkers by methods well known to those skilled in the art, and disclosed for example in U.S. Pat. No. 2,798,053 (Brown). A commercially available polyacrylic acid resin or a commercially available particulate resin such as the CARBOPOL ™ resins discussed above can be used as received if it is available in an appropriate particle size and with a suitably low water content.

Conventional drying methods, preferably using temperatures less than about 95° C., and more preferably less than about 50° C., can be used to dry a resin to the desired degree, e.g., less than about 2% water content. Further, if it is desired to increase or decrease the particle size, a resin can be wet-granulated by first wetting and stirring with a polar solvent (e.g., isopropyl alcohol), drying to the desired degree (e.g., in a tray oven), and then milling to a powder of the desired size. Particle size can also be adjusted by other conventional techniques, with the caveat that substantial degradation of the resin is to be avoided.

To prepare a neutralized resin as discussed above, a particulate polyacrylic acid resin or a particulate covalently crosslinked resin can be suspended by vigorously stirring in a water-soluble solvent (e.g., ethanol, isopropyl alcohol, or methanol). To this suspension, an aqueous solution containing the polyamine or the desired base of a metal can be added. Upon vigorous agitation (e.g., shaking overnight in a conventional laboratory shaker) a homogeneous mixture containing the neutralized resin obtains. Drying this mixture, for example by spray drying, affords a free-flowing powder. With high concentrations of base, a spray drying process can become more time consuming than desired, in which case a wet-granulation process might be preferred. In such a process, the polyacrylic acid resin and the base can first be mixed as solids, then moistened with a polar solvent (e.g., isopropyl alcohol) and stirred. Under such conditions, it is possible that significant neutralization does not occur. However, when the resulting resin is incorporated into a composition of the invention as described below, and the composition is placed on a moist surface such as a mucosal surface, it is possible that further neutralization occurs in situ. For the purposes of the instant specification and claims, a material so made is termed a neutralized resin prior to presumed further in situ neutralization. In any case, the resulting mixture can then be dried to the desired degree and milled using conventional apparatus to form a powder of the desired particle size.

In embodiments wherein the support matrix is an elastomeric component, a suitable resin can then be formulated into a device by a solvent-casting method that involves dispersing the resin, e.g., with stirring, in a solution of an elastomeric component in a volatile organic solvent, such as hexane or toluene, to form a resin/elastomeric component/solvent mixture. A drug and any excipient or other ingredient can be incorporated by first adding it and then the resin, or vice-versa, to a solution of the elastomeric component in a volatile organic solvent. Alternatively, any excipient or other ingredient can be incorporated by first adsorbing it on the resin or on an inert support such as silica, absorbing it into the resin, or ionically binding it to the resin. The device can then be made into a sheet. This can be done by coating (e.g., using a knife coater) a suitable release liner with a uniform thickness of a resin/elastomeric component/solvent mixture containing any excipient or other ingredient and allowing the solvent to be removed without substantial foaming or bubbling caused by solvent release, e.g., by evaporation in air or by drying methods well known to those skilled in the art.

As an alternative that avoids the use of added solvents, the components of a device can be milled together neat using a conventional rubber mill such as a two-roll mill. If the elastomeric component comprises more than one ingredient, these ingredients can be milled together first to form a homogeneous elastomeric component. The polymeric resin and any excipient or other ingredients can then be milled in to form a homogeneous composition of the invention. In some cases it is necessary to heat or cool the rolls in order to assure good mixing and in order to facilitate removal of the device from the rolls. Any excipient or other ingredients can be added neat to the polymeric resin prior to milling. Alternatively, they can be adsorbed on the resin, adsorbed on an inert support such as silica, absorbed into the resin, or ionically bound to the resin by conventional methods prior to milling. The device can then be made into a sheet by pressing between two sheets of release liner in a heated platen press at a pressure of about 35,000 to about 175,000 KPa and at a temperature of about 50° C.

In embodiments wherein the support matrix is a PTFE web, a suitable resin can be formulated into a device according to the general methods set forth in U.S. Pat. No. 4,153,661 (Ree et al.), incorporated herein by reference. Such methods involve the use of an aqueous PTFE formulation. The use of an aqueous PTFE formulation, however, results in severe swelling of the resin and the device sticks to the rolls when it is milled. Moreover, as the devices of the invention contain less than about 9 percent by weight water based on the weight of the resin, drying to the desired level can be difficult and/or time consuming. Accordingly, it is preferred to prepare such embodiments by a method that avoids the use of water or a solvent (such as ethanol) that swells the resin. A preferred method involves combining the resin with dry PTFE particles having an average particle size of about 300 $\mu$m to about 1000 $\mu$m, and adding sufficient inert non-hydroxylic liquid to form a putty-like mass. Preferably, about 100 parts by weight of the resin is used, about 40 parts by weight of the PTFE is used, and about 500 parts by weight of the inert non-hydroxylic liquid is used. Suitable liquids include chlorofluorocarbon and fluorocarbon liquids. Fluorocarbon liquids such as FLUORINERT TM FC5312 electronic fluid (3M) are preferred.

The resulting mixture is then stirred until it is of dough-like consistency and processed in a rubber mill as generally described in U.S. Pat. No. 4,153,661. Generally the processing involves biaxial fibrillation of the PTFE by repeatedly passing the mixture between the calendering rolls of the rubber mill. After each individual pass the resulting sheet is folded parallel to the axis of the calendering rolls into a layered structure, preferably a three-layered structure, rotated 90° and passed again through the calendering rolls. Preferably about 10 to about 20 passes are carried out in order to form a PTFE web having the resin substantially dispersed throughout. The resulting sheet is then passed through the rolls as required in order to form a sheet of the desired thickness. Once a sheet of the desired thickness is made, it can be air-dried at room temperature or placed in a convection oven at an appropriate temperature in order to remove the excess inert liquid.

For embodiments involving an elastomeric support matrix the preferred thickness of the final dry sheet of device is from about 0.3 mm to about 5 mm, more preferably from about 0.8 mm to about 3 mm. For embodiments involving a PTFE web support matrix the final dry sheet of device is preferably 0.2 mm to about 1 mm thick.

Suitable release liners for use in the above-described methods of preparation include conventional release liners comprising a known sheet material, such as a polyester web, a polyethylene web, or a polystyrene web, or polyethylene-coated paper, coated with a suitable silicone-type coating such as Daubert 164-Z release liner (commercially available from Daubert Co., Elmhurst, Ill.).

In embodiments involving an elastomeric support matrix, a backing material can be applied using methods well known to those skilled in the art. The backing material is preferably a flexible film that prevents bulk fluid flow and is inert to the ingredients of the composition. The backing material can be any of the conventional materials used as backing for tapes or dressings, such as polyethylene, polypropylene, ethylene-vinyl acetate copolymer, ethylene propylene diene copolymer, polyurethane, rayon, and the like. Non-woven materials such as polyesters, polyolefins, and polyamides can also be used. Also, a layer of a hydrophobic elastomer can function as a backing. Preferred backing materials include an acrylate pressure-sensitive adhesive coated polyurethane film such as TEGADERM TM brand surgical dressing (commercially available from the 3M Company, St. Paul, Minn.).

A device with a backing applied thereto can be made into a patch with a backing by die-cutting individual patches from the sheet. Alternatively, a patch with no backing can be prepared by die-cutting individual patches from a coated release liner prepared by the solvent method set forth above or by die-cutting from a sheet. A patch can be of any suitable size and shape, e.g., a 1 cm$^2$ circular disk.

In particular embodiments the device has no backing or a backing that is substantially permeable to the bodily fluid with which the composition is in contact (e.g., saliva). In such embodiments, it is preferred that the device exhibit substantially no disintegration over the time period during which the device is intended to remain adhered to the mucosal surface (e.g., about 1 hour).

In other particular embodiments the device has a backing that is substantially impermeable to the bodily fluid with which the composition is in contact. In such embodiments, the backing further protects the device from substantial disintegration over the time period during which the composition is intended to remain adhered to the mucosal surface. (Typically about one hour or less.)

Embodiments wherein the support matrix is a PTFE web exhibit no substantial degradation because the materials from which such webs are made do not swell or degrade under conditions of use. Accordingly, preferred embodiments of this type do not involve a backing.

A device used in the methods of this invention adheres to mucosal surfaces but exhibits substantially no instantaneous adhesion to dry skin. A device can therefore be handled by the user without undue concern that its mucosal adhesive properties will be compromised by the device adhering to skin or another dry surface before it is placed on the mucosal surface.

When a device is in place on the mucosa, it absorbs compounds (e.g., drugs) from the blood. Therefore a device can be applied to a mucosal surface, such as the oral mucosa, e.g., the buccal mucosa or gingival mucosa, of a mammal, allowed to remain in place for a time sufficient to allow the device to absorb a compound in an amount proportional to the blood level of the compound (typically about 0.5-1 hour), and removed in order to measure the amount of compound in the device. The opposing surfaces of a device or a patch with no backing can be adhered to opposing mucosal surfaces, e.g., the gum and the cheek or lip, thereby providing added adhesion and a means of simultaneous drug absorption from two mucosal surfaces into the same patch.

The relative amount of a compound in the blood can be easily determined by placing a device on the mucosa for a designated period of time, removing the device, measuring the concentration of the compound that has been absorbed into the device, and comparing the result to a previous result obtained in the same manner. In order to monitor the absolute blood level of a compound, a device can be calibrated for the particular compound being monitored. This can be done by comparing the actual blood level of a compound in a subject (measured by an established assay) to the concentration of the compound that is absorbed into the device after a designated period of time adhered to the mucosa of the subject, and creating a calibration curve. Exemplary compounds that can be monitored using the methods of the invention include drugs such as steroids (e.g., estradiol), benzamides (e.g., flecainide), and xanthines (e.g., theophylline). Others that are known to pass mucous membranes can also be monitored, such as morphine alkaloids (morphine, heroin) and cocaine.

The procedures set forth below describe non-limiting methods of preparing partially neutralized resins suitable for use in a device.

PREPARATIVE METHOD 1

CARBOPOL TM 934 P resin (200 g) and calcium hydroxide (15 g, particle size about 25 μm) were placed in a 5 quart Hobart mixer (Model N-50, Hobart Corp., Troy, Ohio) and mixed for 5 minutes at a setting of 1. Stirring was continued and isopropyl alcohol (about 200 mL) was added dropwise to the mixture over a period of about 5 minutes, resulting in a material of a dough-like consistency. This material was dried overnight in a tray oven at 90° C., and milled in a small mill (Fitzpatrick Model J, Fitzpatrick Co., Elmhurst, Ill.) to afford a resin in the form of a powder with a particle size of about 30-50 μm.

PREPARATIVE METHOD 2

CARBOPOL TM 934 P resin (10 g) was added slowly to ethyl alcohol (500 mL). The resulting mixture was stirred vigorously with a magnetic stirrer until the resin was homogeneously suspended. An aqueous solution of calcium hydroxide (780 mL of a solution containing 1 g/L, 780 mg) was added and the mixture was placed in a screw top jar. The jar was placed in an Eberbach laboratory shaker and shaken overnight at room temperature. The resulting mixture was spray dried using a Buchi Model 190 Mini-Spray Drier (Buchi Laboratories, Flawil, Switzerland). A free-flowing powder (5 g) resulted.

PREPARATIVE METHOD 3

CARBOPOL TM 934 P resin (10 g) was added slowly to ethyl alcohol (500 mL). The resulting mixture was stirred vigorously until the resin was homogeneously suspended. An aqueous solution of aluminum hydroxide (0.91 g in 600 mL water) was added, and the mixture was stirred and dried as set forth in Preparative Method 2.

PREPARATIVE METHOD 4

CARBOPOL TM 934 P resin (300 g) and calcium hydroxide (38 g, particle size about 25 μm) were placed in a 5 quart Hobart mixer and mixed for about 5 minutes at a setting of 1. Stirring was continued and isopropyl alcohol (about 300 mL) was added dropwise over a period of about 5 minutes. The resulting material was dried and milled according to Preparative Method 1 to afford a resin in the form of a powder with a particle size of about 30-50 μm.

The following illustrates preparation of devices useful in the methods of the invention. All parts and percentages are by weight unless otherwise indicated.

DEVICE 1

A solution containing a polyisobutylene with a viscosity average molecular weight of about 53,000 (1.6 g, as 3.2 g of a stock solution containing 50% by weight VISTANEX TM LM-MH polyisobutylene, commercially available from Exxon Chemical Co., Houston, Tex., in a 1:1 mixture by volume of hexane and toluene) and a polyisobutylene with a viscosity average molecular weight of about 1,200,000 (0.080 g, as 0.4 g of a stock solution containing 20% by weight of VISTANEX TM L-100 polyisobutylene, also commercially available from Exxon Chemical Co., in a 1:1 mixture by volume of hexane and toluene) was prepared. Resin obtained from Preparative Method 2 (3.0 g) was added with stirring. A 1:1 solution of hexane and toluene (5 mL) was added and stirring continued for about 5 minutes. The mixture was then coated using a knife coater onto silicone-coated release liner at a wet thickness of 3.4 mm. The solvent was allowed to evaporate. A backing material, TEGADERM TM 1625 surgical dressing, was applied by hand to the exposed surface of the coating to provide a device having a backing material applied thereto. Individual patches were hand-cut from this sheet material with a 1 cm² circular die.

DEVICES 2-12

Using the general method used to prepare Device 1, 5.0 g samples of the compositions set forth in TABLE I below were prepared. All amounts are based upon the total weight of the composition. Individual patches were prepared according to the general method used to prepare Device 1 and remained adhered to human buccal mucosa for a study period indicated in TABLE I. The study period was terminated by removing the patch by hand. No entry indicates that the patch was adhered but was removed after a short time.

TABLE I

| COMPONENT | DEVICE (wt %) | | | | | |
|---|---|---|---|---|---|---|
| | 2 | 3 | 4 | 5 | 6 | 7 |
| CARBOPOL ™ 910 | 50 | 60 | 40 | — | — | — |
| CARBOPOL ™ 934P | — | — | — | — | — | 60 |
| CARBOPOL ™ 940 | — | — | — | 60 | — | — |
| CARBOPOL ™ 941 | — | — | — | — | 60 | — |
| CARBOPOL ™ 951 | — | — | — | — | — | — |
| CARBOPOL ™ 1342 | — | — | — | — | — | — |
| VISTANEX ™ LMMH | 40 | 32 | 48 | 32 | 32 | 32 |
| VISTANEX ™ L100 | 10 | 8 | 12 | 8 | 8 | 8 |
| Study Period | 24 h | 24 h | — | 2 h | 2 h | 24 h |

| | 8 | 9 | 10 | 11 | 12 |
|---|---|---|---|---|---|
| CARBOPOL ™ 910 | — | — | — | — | — |
| CARBOPOL ™ 934P | 50 | 40 | — | — | — |
| CARBOPOL ™ 941 | — | — | — | — | — |
| CARBOPOL ™ 951 | — | — | 40 | 60 | — |
| CARBOPOL ™ 1342 | — | — | — | — | 60 |
| VISTANEX ™ LMMH | 40 | 48 | 48 | 32 | 32 |
| VISTANEX ™ L100 | 10 | 12 | 12 | 8 | 8 |
| Study Period | 24 h | — | 20 h | 24 h | 4 h |

The data in TABLE I show that these patches adhere to human oral mucosa.

DEVICES 13-16

CARBOPOL ™ 910 resin (100 g) was placed in a Hobart mixer (Model N-50, Hobart Corp., Troy, Ohio) and mixed at a setting of 1 while isopropyl alcohol (100 ml) was added dropwise over a period of about 5 minutes. The resulting material was dried overnight in a tray oven at 32° C. and milled in a small mill (Fitzpatrick Model J, Fitzpatrick Co., Elmhurst, Ill.) to afford CARBOPOL ™ 910 resin with an average particle size of about 30 μm to 50 μm Using the general method used to prepare Device 1, and the CARBOPOL ™ 910 resin as processed above, 5.0 g samples of the compositions set forth in TABLE II were prepared. All amounts are based upon the total weight of the composition. Individual patches were prepared according to the general method used to prepare Device 1 and remained adhered to human buccal mucosa for a study period of about 20 hours. The study period was terminated by removing the patch by hand.

TABLE II

| Device No. | % CARBOPOL ™ 910 | % VISTANEX ™ LM-MH | % VISTANEX ™ L-100 |
|---|---|---|---|
| 13 | 50 | 40 | 10 |
| 14 | 60 | 32 | 8 |
| 15 | 70 | 24 | 6 |
| 16 | 75 | 20 | 5 |

DEVICES 17-19

Using the general method used to prepare Device 1, 5.0 g samples of the compositions set forth in TABLE III below were prepared. All amounts are based upon the total weight of the composition. The polyacrylic acid samples were purchased from Polysciences, Inc., Warrington, Pa. Individual patches were prepared according to the general method used to prepare Device 1 and remained adhered to human buccal mucosa for a study period of about 4 hours. The study period was terminated by removing the patch by hand.

TABLE III

| Device No. | % Polyacrylic Acid (MW) | % VISTANEX ™ LMMH | % VISTANEX ™ L100 |
|---|---|---|---|
| 17 | 50 (450,000) | 40 | 10 |
| 18 | 50 (1,000,000) | 40 | 10 |
| 19 | 50 (4,000,000) | 40 | 10 |

DEVICE 20

A solution (5.0 g) containing 70% by weight toluene, 10% by weight mineral oil, and 20% by weight of Kraton ™ D 1107 rubber was prepared. Polycarbophil (Biomimetics, Inc., Lexington, Mass.) was added over a period of about 5 minutes with stirring. Patches were made from the resulting mixture as described above in connection with Device 1. The patches remained strongly adhered to human buccal mucosa for a study period of several minutes. The study period was terminated by removing the patch by hand.

DEVICES 21 and 22

A copolymer of 96% by weight isooctylacrylate and 4% by weight acrylamide (prepared according to the method of Example 2 of U.S. Pat. No. 4,751,087 (Wick), the entire disclosure of which is incorporated herein by reference) was dissolved in a 90:10 (V/V) solution of ethyl acetate in methanol in an amount sufficient to prepare a 30% by weight solution of the copolymer. To an aliquot of the solution was added with stirring polycarbophil (Biomimetics, Inc., Lexington, Mass.) in an amount sufficient to prepare the compositions set forth in TABLE IV below.

TABLE IV

| Device | % Elastomer | % polycarbophil |
|---|---|---|
| 21 | 25 | 75 |
| 22 | 20 | 80 |

The compositions of TABLE IV were made into patches according to the general method used to prepare Device 1. The patches remained adhered strongly to human buccal mucosa for a study period of about 2 hours. The study period was terminated by removing the patch by hand.

DEVICES 23–30

Compositions were prepared by milling the components listed in TABLE V at room temperature in a two-roll mill (Reliable Mill Model 3216, Rubber and Plaster Machine Company, North Bergen, N.J.) according to the general method set forth below.

The lower molecular weight component of the elastomer was added to the mill and milled until it was distributed on the rollers. The higher molecular weight component of the elastomer was then added as small pieces and milling was continued until a homogeneous mixture obtained. The plasticizer (if any) was then added and the mixture was milled until homogeneous.

The resin was added slowly to the elastomeric component in the mill and this mixture was milled until a uniform composition obtained. It was necessary to periodically remove the material from the rollers, form it into a ball and re-mill to ensure a uniform composition. The composition was removed from the mill by scraping the rollers.

About 15 to 25 g of the composition was pressed at about 70,000 KPa between two 17 cm × 17 cm pieces of silicone-coated release liner in a platen press heated to about 50° C. to afford a laminate comprising a sheet of composition about 2 mm thick. Individual patches were cut from the resulting laminate with a die.

Devices were prepared as described above using the components set forth in TABLE V below. Individual patches were found to adhere to human oral mucosa.

TABLE V

| Component | Device Number | | | | | | | |
|---|---|---|---|---|---|---|---|---|
| | 23 | 24 | 25 | 26 | 27 | 28 | 29 | 30 |
| polycarbophil* | 30 g | 30 g | 30 g | | | 30 g | 30 g | 30 g |
| CARBOPOL TM 934-P | | | | 90 g | 35 g | | | |
| LIR-50** | 12 g | | | | | | | |
| LIR-410** | | 12 g | | | | | | |
| LIR-506** | | | 12 g | | | | | |
| VISTANEX TM L-100 | 8 g | 8 g | 8 g | | 9.8 g | 4 g | 4 g | 4 g |
| VISTANEX TM L-80 | | | | 30 g | | | | |
| VISTANEX TM LM-MH | | | | | 4.5 g | 16 g | 16 g | 16 g |
| mineral oil | | | | | | 3 g | | |
| corn oil*** | | | | | | | 3 g | |
| silicone oil**** | | | | | | | | 3 g |

*from Biomimetics, Inc., Lexington, MA
**from Arakawa Chemical, Chicago, IL
***Mazola TM Corn Oil
****Dow Corning 200 fluid, 200 cps

DEVICES 31–32

Compositions were prepared by milling at room temperature in a two-roll mill (Model Number 53060 Farrell-Birmingham Ansonia Conn.) with rollers of 15 cm diameter and 30 cm length according to the general method set forth below. The polyisobutylene or, in the case of a two-component polyisobutylene elastomeric component, the higher molecular weight polyisobutylene component was added to the mill in portions and milled until uniform (about 15 minutes) and rolled into a sheet. The sheet was placed in the mill, and the resin or, in the case of a two-component polyisobutylene elastomeric component, the resin and the lower molecular weight polyisobutylene component together were added slowly and milled until a uniform composition obtained. The composition was then rolled out of the mill in the form of a sheet by adjusting the space between the rollers such that a sheet of the desired thickness (e.g., 1–2 mm) was produced. Individual patches were cut from the resulting sheet with a 1 cm$^2$ circular die.

Compositions were prepared as described above using 25 weight percent VISTANEX TM L-80 polyisobutylene and 75 weight percent CARBOPOL TM 934P resin (Device 31) and 20 weight percent VISTANEX TM L-110 polyisobutylene, 10 weight percent VISTANEX TM LM-MH polyisobutylene, and 70 weight percent CARBOPOL TM 934P resin (Device 32).

Patches of the compositions of Devices 31 and 32 remained adhered to human buccal mucosa for a study period of about 8 hours and about 15 hours, respectively. The study periods were terminated by removing the patches by hand.

DEVICE 33

CARBOPOL TM 910 resin (50 g) was mixed with 16.7 g of PTFE (TEFLON TM 6-C polytetrafluoroethylene, DuPont) and 250 g of FLUORINERT TM 5312 electronic liquid (3M) to afford a substantially homogeneous putty-like mass. This mass was further mixed by hand with a spatula for about 1 minute. The mass was then formed into a film by 15 successive passes between steel calendering rolls (15 cm in diameter, 28 cm long) at 50° C. using a nip gap of about 4 mm. After each pass, the resulting substantially rectangular film was z-folded parallel to the axis of the calendering rolls and rotated 90° prior to the next pass. After these 15 initial passes the film was again repeatedly passed through the rolls, beginning with a nip gap of about 4 mm and closing the nip gap about 0.65 mm on each successive pass until the final sheet of device was about 0.3 mm thick. The final sheet of device was air-dried at room temperature to remove the excess liquid. Patches of about 1 cm$^2$ area were cut from the sheet with a 1 cm$^2$ circular die.

The following EXAMPLES are provided to illustrate the methods of the invention and are not intended to be limiting thereof.

EXAMPLE 1

A device prepared according to the method described in connection with Device 33 above in the form of a circular patch with an area of about 1 cm$^2$ was adhered to the inside of the upper lip of an asthmatic human volunteer who was routinely taking large doses of the bronchodilator drug theophylline. On the study day, a patch was applied to the volunteer at 8:00 am, 9:00 am, 1:00 p.m., and 2:00 p.m.. Each patch was allowed to adhere to the mucosal membrane of the upper lip for one hour, after which time it was removed, placed into a glass vial and stored frozen until analysis. At the time of patch collection, a blood sample and a saliva sample were also collected.

Plasma and saliva concentrations of theophylline were determined by TDx TM assay (Abbott Laboratories). Theophylline concentration in the patches was determined by incubating the patches for about 6 hours at about 35° C. in 5 mL of HPLC mobile phase (0.01 M acetate buffer/methanol/tetrahydrofuran in volume ratio of 92:7:1) and injecting an aliquot directly onto the column (20 cm, Hypersil TM 5 $\mu$m octadecylsilane, (Shandon Southern Products Ltd., Div. Phicom, Cheshire, England). No interfering substances from the patches were noted on the chromatograms. Patch concentrations of theophylline were approximately one-half of corresponding plasma levels; the correlation coefficient ($r^2$) of patch levels ($\mu$g/g) vs. plasma levels ($\mu$g/mL) was 0.9. Plasma protein binding of theophylline in human plasma is generally thought to be 50% to 60%. Therefore, patch concentrations of theophylline in this example approximate actual levels of free (unbound) theophylline in blood.

EXAMPLE 2

After dosing each of four laboratory beagle dogs with 100 mg of theophylline, two patches made as described in connection with Device 33 above were adhered to the mucosal side of the upper lip of each dog at 1.0, 1.5, 3.0, 3.5, 7.0, and 7.5 hours postdose. Of each set of two patches, one was removed 0.5 hours after application and one was removed 1.0 hours after application. At 0.5 hours after application, the patches were usually still tightly adhered and much more difficult to remove than at 1.0 hours after application. The patches were placed in a glass vial and stored frozen until the time of analysis. Blood samples were collected from each dog at 2, 4, and 8 hours postdose for analysis of plasma theophylline levels. Concentrations of theophylline in the patches were determined by HPLC assay as described in EXAMPLE 1 above and plasma levels were determined by TDx TM assay (Abbott Laboratories). The correlation of patch theophylline levels with plasma theophylline levels was somewhat better for the 1.0 hours patches compared with the 0.5 hour patches. In general, patch theophylline concentrations ranged from about 0.3 to 0.7 times the corresponding plasma concentrations. The correlation coefficients, $r^2$, for patch theophylline versus plasma theophylline concentrations at 2, 4, and 8 hours postdose were 0.719, 0.928, and 0.769, respectively.

EXAMPLE 3

After dosing 1 female beagle dog with 5 mg/kg of $^{14}$C-labeled flecainide acetate, a 1 cm$^2$ circular patch made as described in connection with Device 33 above was adhered to the mucosal side of the upper lip of each dog at ½, 1½, 2½, 4½, 5½, 6½, 22½, and 26½ hours post dose. Each patch was allowed to adhere for about 1 hour after which time the patches were removed and allowed to dry. At the time of patch collection, blood samples were also taken.

The total radioactivity retained in each patch was measured by combusting the patch in a Packard Model 306 Biological Oxidizer (Hewlett Packard), capturing the $^{14}$CO$_2$ in a scintillation cocktail, and determining total radioactivity by liquid scintillation spectrometry. Blood levels of radioactivity were similarly determined and found to show a good linear correlation with the corresponding patch levels.

EXAMPLE 4

In a manner similar to that used in EXAMPLE 3 above, patch and plasma levels of radiolabeled estradiol were measured and found to show a good linear correlation.

EXAMPLE 5

Using the general method described above in connection with Device 1, patches comprising 60% by weight of polycarbophil, 32% by weight of VISTANEX TM LM-MH polyisobutylene and 8% by weight of VISTANEX TM L-100 polyisobutylene were prepared. After orally dosing a beagle dog with 400 mg of theophylline (SLO-BID TM theophylline available from Rorer Pharmaceuticals, Fort Washington, Pa.), a patch was adhered to the mucosal side of the upper lip at 2, 3, 4, 6, and 8 hours post dose. Each patch was removed 1 hour after application. The patches were placed in glass vials and frozen. Blood samples were collected at 2, 3, 4, 5, 6, 8 and 10 hours post dose for analysis of plasma theophylline levels.

Plasma concentrations of theophylline were determined by TDx TM assay. Theophylassay line concentration in the patches was determined in the following manner. The patches were allowed to dry for 3 days at ambient conditions then each patch was placed in a glass conical test tube. A 5 mL portion of 5% isopropanol in chloroform was added to the tube and the tube was placed in a sonic bath for approximately 1 hour. The tube was centrifuged and the extract was pipetted into a glass tube. The procedure was repeated and the combined extracts were taken to dryness under a stream of nitrogen. A 1 mL portion of fresh, blank dog plasma was added to the residue in the tube and vortexed. An aliquot of plasma from each patch was assayed for theophylline by TDx TM assay. Patch theophylline concentrations ranged from 0.3 to 0.8 times the corresponding plasma concentrations.

EXAMPLE 6

A patch prepared according to the method described above in connection with Device 33 comprising about 75% by weight of polycarbophil in a web of TEFLON TM polytetrafluoroethylene was tested according to the method of EXAMPLE 5. Patch theophylline concentrations ranged from 0.4 to 1 times the corresponding plasma levels.

The claimed invention is:

1. A method of measuring the blood level of a drug in a mammal, comprising the steps of:
    a) adhering a device to a mucosal surface of a mammal, which device comprises:
        (i) a particulate polymeric resin comprising at least about 55% by weight of carboxylic acid moieties based on the total weight of the polymeric resin, and
        (ii) about 10 to about 200 parts by weight of a hydrophobic support matrix, based on 100 parts by weight of the resin,
    wherein the resin is dispersed substantially throughout the support matrix, and which is substantially free of drug, contains less than about 9% water by weight based on the weight of the polymeric resin, exhibits substantially no instantaneous adhesion to dry skin, and adheres to a mucosal surface;
b) allowing the device to remain adhered for a time sufficient to allow the device to absorb the drug in an amount proportional to the blood level of the drug;
c) removing the device;
d) measuring the amount of the drug in the device; and
e) correlating the amount of the drug in the device to the blood level of the drug.

2. A method of measuring the relative blood level of a drug in a mammal, comprising the steps of:
a) adhering a device to a mucosal surface of a mammal which device comprises:
(i) a particulate polymeric resin comprising at least about 55% by weight of carboxylic acid moieties based on the total weight of the polymeric resin, and
(ii) about 10 to about 200 parts by weight of a hydrophobic support matrix, based on 100 parts by weight of the resin,
wherein the resin is dispersed substantially throughout the support matrix, and which is substantially free of drug, contains less than about 9% water by weight based on the weight of the polymeric resin, exhibits substantially no instantaneous adhesion to dry skin, and adheres to a mucosal surface;
b) allowing the device to remain adhered for a predetermined period of time;
c) removing the device;
d) measuring the amount of the drug in the device; and
e) comparing the result from step d) to a previous result obtained in the same manner.

3. A method according to claim 1, wherein the device when placed on the mucosal surface is free of drug.

4. A method according to claim 1, wherein the support matrix component of the device is a polytetrafluoroethylene web.

5. A method according to claim 1, wherein the polymeric resin component of the device consists essentially of acrylic acid monomer units.

6. A method according to claim 5, wherein the resin component of the device is covalently crosslinked with about 0.75% to about 2% by weight based on the total weight of the resin of a polyalkenyl polyether.

7. A method according to claim 1, wherein the resin component of the device has an average particle size of between about 1 μm and about 100 μm.

8. A method according to claim 1, wherein the resin component of the device has an average particle size of between about 2 μm and about 10 μm.

9. A method according to claim 1, wherein the device comprises about 50 to about 100 parts by weight of the support matrix based on 100 parts by weight of the resin.

10. A method according to claim 1, wherein up to about 30% of the carboxylic acid moieties of the resin component of the device are neutralized by a base.

11. A method according to claim 10, wherein the base is selected from the group consisting of Al(OH)$_3$ and Ca(OH)$_2$.

12. A method according to claim 10, wherein the base is a polyamine.

13. A method according to claim 1, wherein the device comprises about 15 to about 50 parts by weight of the support matrix based on 100 parts by weight of the resin.

14. A method according to claim 1, wherein the device contains less than about 4% water by weight based on the total weight of the resin.

15. A method according to claim 1, wherein the device contains less than about 2% water by weight based on the total weight of the resin.

16. A method according to claim 1, wherein the support matrix component of the device is an elastomeric component.

17. A method according to claim 1, wherein the support matrix component of the device is a hydrocarbon.

18. A method according to claim 1, wherein the support matrix component of the device comprises a block styrene-butadiene-styrene copolymer, a block styrene-isoprene-styrene isoprene-styrene copolymer, a polyisobutylene, an isoprene rubber, a carboxy-functional polyisoprene, a hydroxy-functional polyisoprene, an acrylate elastomer, or a mixture of two or more of the foregoing.

19. A method according to claim 18, wherein the support matrix component of the device further comprises a plasticizer.

20. A method according to claim 16, wherein the support matrix component of the device is a mixture comprising about 5% to about 50% by weight of a polyisobutylene with a viscosity average molecular weight between about 500,000 and about 2.5 million, and about 50% to about 95% by weight of a polyisobutylene with a viscosity average molecular weight between about 40,000 and about 100,000.

21. A method according to claim 16, wherein the support matrix component of the device is a mixture comprising about 15% to about 25% by weight of a polyisobutylene with a viscosity average molecular weight between about 500,000 and about 2.5 million, and about 75% to about 85% by weight of a polyisobutylene with a viscosity average molecular weight between about 40,000 and about 100,000.

22. A method according to claim 16, wherein the support matrix component of the device is a mixture comprising about 20% by weight of a polyisobutylene with a viscosity average molecular weight between about 500,000 and about 2.5 million, and about 80% by weight of a polyisobutylene with a viscosity average molecular weight between about 40,000 and about 100,000.

23. A method according to claim 16, wherein the support matrix component of the device is a mixture comprising about 20% by weight of a polyisobutylene with a viscosity average molecular weight about 1.25 million and about 80% by weight of a polyisobutylene with a viscosity average molecular weight about 53,000.

24. A method according to claim 16, wherein the device is made by a process comprising the steps of:
(1) adding the constituent or constituents of the elastomeric component to a mill;
(2) milling the constituent or constituents to form a substantially homogeneous elastomeric component;
(3) milling the particulate polymeric resin and the homogeneous elastomeric component from step (2) to form a substantially homogeneous composition.

25. A method according to claim 24, wherein the constituents of the elastomeric component of the device are: about 5% to about 50% by weight of a polyisobutylene with a viscosity average molecular weight between about 500,000 and about 2.5 million; and about 50% to about 95% by weight of a polyisobutylene with a viscosity average molecular weight between about 40,000 and about 100,000.

26. A method according to claim 24, wherein the constituents of the elastomeric component of the device are: about 15% to about 25% by weight of a polyisobutylene with a viscosity average molecular weight between about 500,000 and about 2.5 million, and about 75% to about 85% by weight of a polyisobutylene with a viscosity average molecular weight between about 40,000 and about 100,000.

27. A method according to claim 24, wherein the constituents of the elastomeric component of the device are: about 20% by weight of a polyisobutylene with a viscosity average molecular weight between about 500,000 and about 2.5 million, and about 80% by weight of a polyisobutylene with a viscosity average molecular weight between about 40,000 and about 100,000.

28. A method according to claim 24, wherein the constituents of the elastomeric component of the device are: about 20% by weight of a polyisobutylene with a viscosity average molecular weight about 1.25 million and about 80% by weight of a polyisobutylene with a viscosity average molecular weight about 53,000.

29. A method according to claim 24, wherein the constituents of the elastomeric component of the device are: about 60% to 100% of a polyisobutylene with a viscosity average molecular weight of about 750,000 to about 1,100,000 and 0% to about 40% of a polyisobutylene with a viscosity average molecular weight of about 40,000 to about 100,000.

30. A method according to claim 1 wherein the device has a flexible film backing applied thereto.

* * * * *

UNITED STATES PATENT AND TRADEMARK OFFICE
CERTIFICATE OF CORRECTION

PATENT NO. : 5,113,860
DATED : May 19, 1992
INVENTOR(S) : Roy L. McQuinn

It is certified that error appears in the above-identified patent and that said Letters Patent is hereby corrected as shown below:

Col. 4, Line 21, "polyoefins" should read --polyolefins--.

Col. 16, line 28, "Theophylassay line" should read --Theophylline--.

Col. 18, line 19, the second "isoprene-styrene" should be deleted.

Signed and Sealed this

Twenty-seventh Day of September, 1994

Attest:

BRUCE LEHMAN

Attesting Officer

Commissioner of Patents and Trademarks